(12) United States Patent
Alessi et al.

(10) Patent No.: US 6,180,834 B1
(45) Date of Patent: Jan. 30, 2001

(54) PROCESS FOR THE EXTRACTION OF THE SALTS CONTAINED IN THE NEUTRALIZED SEPARATED PRODUCT OBTAINED IN THE PREPARATION OF PHENOL BY THE OXIDATION OF CUMENE

(75) Inventors: Vanni Alessi, Roncoferrato; Renzo Penzo, Mantova, both of (IT)

(73) Assignee: Enichem S.p.A., San Donato Milanese (IT)

( * ) Notice: Under 35 U.S.C. 154(b), the term of this patent shall be extended for 0 days.

(21) Appl. No.: 09/288,281

(22) Filed: Apr. 8, 1999

(30) Foreign Application Priority Data

Apr. 23, 1998 (IT) .............................. MI98A0864

(51) Int. Cl.$^7$ ................................... C07C 37/68
(52) U.S. Cl. ............................................ 568/754
(58) Field of Search .............................. 568/754

(56) References Cited

U.S. PATENT DOCUMENTS

| | | | |
|---|---|---|---|
| 2,679,535 | * 5/1954 | Lavender | 568/754 |
| 2,734,085 | * 2/1956 | Adams | 568/754 |
| 2,881,222 | * 4/1959 | Joris | 568/754 |
| 3,180,897 | * 4/1965 | Sodomann | 568/754 |
| 4,973,766 | * 11/1990 | Penzo | 568/754 |
| 5,658,437 | 8/1997 | Alessi et al. . | |
| 5,811,598 | 9/1998 | Alessi et al. . | |

FOREIGN PATENT DOCUMENTS

| | | |
|---|---|---|
| 0 717 024 | 6/1996 | (EP) . |
| 743004 | 1/1956 | (GB) . |

* cited by examiner

*Primary Examiner*—Michael L. Shippen
(74) *Attorney, Agent, or Firm*—Oblon, Spivak, McClelland, Maier & Neustadt, P.C.

(57) ABSTRACT

Process for the extraction of the salts contained in the neutralized separated product obtained in the preparation of phenol by the oxidation of cumene, wherein the flow-rate of the aqueous stream of the separation section of cumene hydroperoxide is reduced by substituting the stream of fresh water used for washing the neutralized separated product, generally obtained by the demineralization of well or running water, with process water taken from another section of the production plant.

4 Claims, 1 Drawing Sheet

PROCESS FOR THE EXTRACTION OF THE SALTS CONTAINED IN THE NEUTRALIZED SEPARATED PRODUCT OBTAINED IN THE PREPARATION OF PHENOL BY THE OXIDATION OF CUMENE

The present invention relates to a process for the extraction of the salts contained in the neutralized separation product obtained in the preparation of phenol by the oxidation of cumene.

More specifically, the present invention relates to a process for the reduction of water consumption in washing the neutralized separation product obtained in the production of phenol by the oxidation of cumene.

It is known that phenol can be prepared from cumene, as described in "Ullmann's Encyclopedia of Industrial Chemistry", Fifth Edition, 1991, Vol. A 19, 302, according to a process which is substantially developed in two steps. The first relates to the oxidation of cumene to cumene hydroperoxide, the second relates to the separation of cumene hydroperoxide to phenol and acetone carried out in the presence of an acid catalyst. The separated product is then subjected to distillation to recover the phenol and acetone.

In the production process of phenol from cumene a large quantity of water is normally adopted, partly used as solvent of the chemical products which must be added to the main streams to obtain optimum process conditions, or for the recovery of phenol from organic streams from which it would be very difficult to obtain by distillation. Or, the water is used as such as solvent in washing operations whose purpose is to reduce as much as possible the concentration of saline compounds in the organic streams to be sent for distillation.

Examples of the first type of water use are aqueous solutions of $Na_2CO_3$ (or NaOH) added to oxidation reactors to stabilize the pH; the aqueous solution of $H_2SO_4$ added as catalyst to separation reactors of cumene hydroperoxide to phenol and acetone; the aqueous solution of NaOH used to salify the phenol contained in the hydrocarbon stream which is separated in the distillation section of the separated product.

Examples of the second type of water use are represented by the washing of the oxidated product, to eliminate the possible presence of $Na_2CO_3$ (or NaOH) and sodium salts of the organic acids formed during the oxidation reaction or the washing of the neutralized separated product to eliminate possible traces of $Na_2SO_4$ and the salts of organic acids dissolved therein, before it is sent to the distillation section for the recovery of the phenol and acetone.

The presence of water can also be found in other parts of the production process, for example in the liquid ring compressors or ejectors for effecting the vacuum necessary for the distillation columns.

Finally a certain quantity of water derives from the repeated flushing operations of the lines, the washing of the equipment and possible recovery of rain water, should this be polluted.

These aqueous streams form the process water whose overall amount corresponds more or less to the same quantity of phenol produced. They are subdivided into two main streams with an almost equal flow-rate, which are recovered from the oxidation section of cumene and from the separation section of cumene hydroperoxide, respectively.

The aqueous streams may contain organic compounds, in particular phenol and acetone, and must therefore be treated before being sent for biological purification to reduce the loss of high-quality products to the minimum. As a result, the greater the quantity of water fed/recovered in the plant, the more dilute will be the compounds to be recovered and the more expensive their recovery from the aqueous stream. It is therefore convenient for the quantity of water fed to the plant to be as small as possible.

The purpose of the present invention is to contribute to reducing the quantity of water used in the production process of phenol by the oxidation of cumene.

More specifically, the objective of the present invention is to reduce the flow-rate of the aqueous stream of the separation section of cumene hydroperoxide, by substituting the stream of fresh water used for washing the neutralized separated product, generally obtained by the demineralization of water coming from wells or running waters, with process water taken from another section of the production plant.

The present invention therefore relates to a process for the extraction of the salts contained in the neutralized separated product obtained in the preparation of phenol by the oxidation of cumene which comprises:

a) feeding the separated product essentially consisting of a stream of phenol and acetone in continuous to an extraction/washing with water section so as to obtain a first aqueous stream containing the extracted products and a first organic stream containing acetone, cumene, phenol and other organic products (for example α-methylstyrene);

b) feeding said first organic stream, together with a second recycled aqueous stream containing acetone, to a mixing section;

c) feeding the stream leaving the mixing section to a first decanting system to obtain a second organic stream and a third aqueous stream;

d) feeding said third aqueous stream, substantially without acetone (about 10% by weight), to the washing section of step (a);

e) feeding said second organic stream to a distillation section to obtain a stream of heavy products essentially consisting of phenol and a stream of light products essentially consisting of water, acetone and hydrocarbons (cumene and α-methylstyrene);

f) feeding the stream of light products to a second decanting system to obtain a third organic stream essentially consisting of acetone and hydrocarbons, and the second aqueous stream which is totally or partially recycled to the mixer of step (b).

Figure 1:
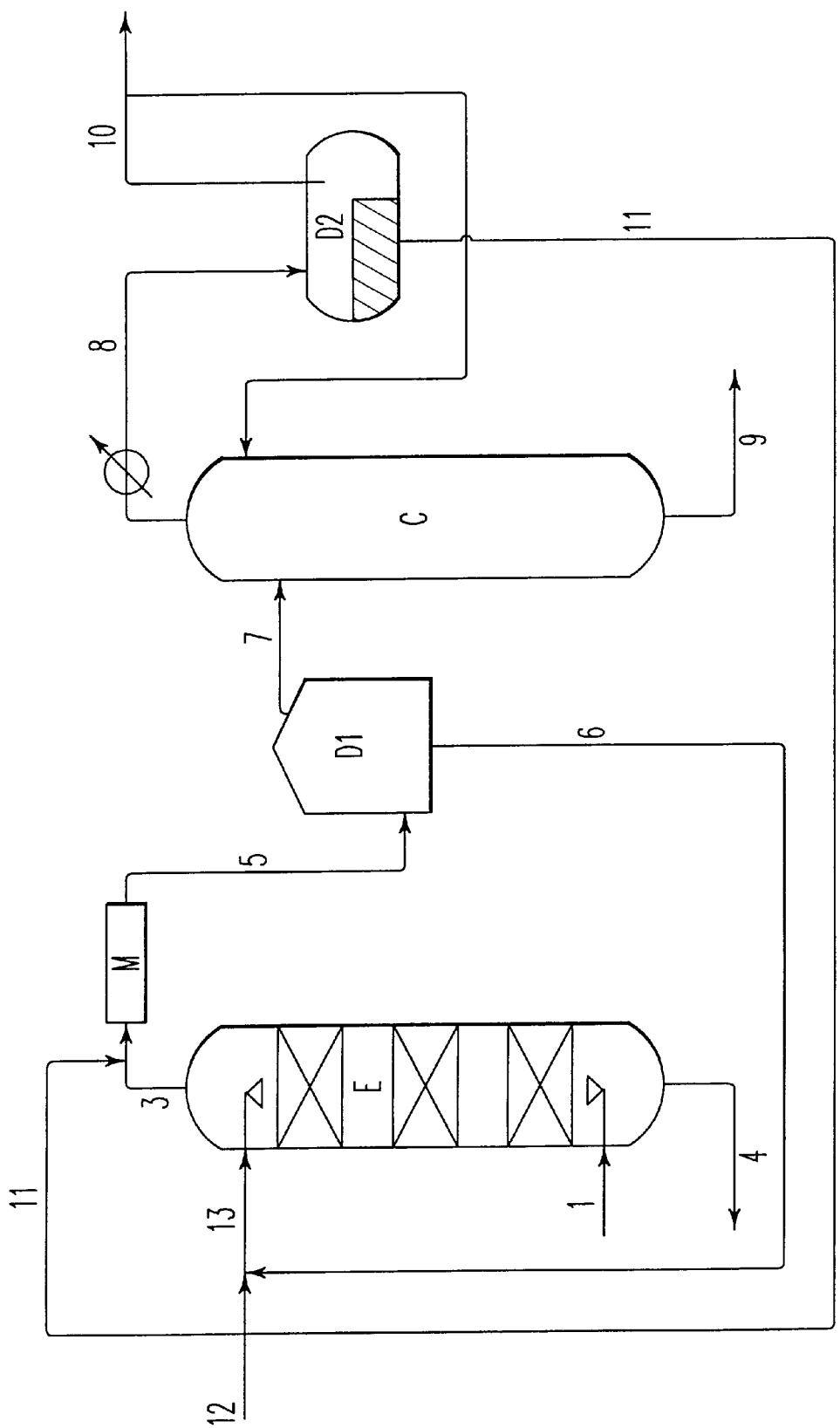
FIG. 1 shows a block diagram of the reactor for the extraction of salts contained in the neutralized separated product obtained in the preparation of phenol by the oxidation of cumene.

In the separation of cumene hydroperoxide, the latter is transformed into phenol and acetone by reaction catalyzed by acids, in particular sulfuric acid. In the product fed to the reaction, in addition to cumene hydroperoxide, by-products formed during the oxidation reaction are also present, which, in the presence of the acid catalyst, react with each other and with phenol or acetone reducing the yield to useful products. For example, 2-phenyl-propanol-2 (a typical by-product of the oxidation of cumene) in the presence of the acid catalyst dehydrates to α-methylstyrene which reacts with itself forming dimers or with phenol forming cumyl-phenols. To prevent the presence of acid causing secondary reactions, the reaction product must be neutralized before being sent for distillation.

To neutralize the acid catalyst a quantity stoichiometrically equivalent to a base, for example NaOH or a sodium salt of a weak acid, for example sodium phenate, may be sufficient.

The reaction mixture is subsequently sent to a separator where two streams are obtained: one, aqueous, containing sodium sulfate, sodium salts of organic acids and reduced quantities of acetone and phenol; the other, organic, containing phenol and acetone, other organic compounds, water and reduced quantities of sodium salts.

The presence of sodium salts in the organic stream is of such an entity as to determine an $Na^+$ level normally within the range of 30–150 mg/l. The presence of these salts may cause harmful fouling of the reboilers of the distillation columns used for the separation of phenol from acetone. In addition, they are concentrated in the process tails which are recovered as fuel, creating problems relating to fouling of the boilers and the presence of powders in the gaseous effluents discharged into the atmosphere. It is therefore necessary for the organic stream coming from the separation of cumene hydroperoxide to be subjected to washing with water to completely eliminate the sodium sulfate, if present, and reduce the concentration of $Na^+$, deriving from the presence of organic acid salts, to below 5 mg/l.

The washing/extraction of the neutralized separated product is effected in countercurrent using one or more mixer-settlers or, alternatively, a multi-step extractor (filling column, Kuhni column, rotating disk or pulsating column, etc.) and a quantity of water ranging from 5 to 10% of the flow-rate of the organic stream. The water, after washing, is discharged and sent to the water treatment section (first aqueous stream). In the process of the present invention the water used for the washing comes from other recovery sections, for example from the ejectors for reducing the pressure in the distillation columns and/or from the distillation section of the organic product, even if containing a high quantity of acetone.

The organic stream, after washing, is mixed with a second recycled aqueous stream coming from the distillation section and containing acetone.

In particular, the second aqueous stream essentially consists of 50–65% by weight of water and 35–50% by weight of acetone, in addition to traces of phenol and other organic compounds. This stream, not containing saline compounds, can be used as washing water in the corresponding section of the present process. However, the presence of acetone in such high quantities reduces its density to such a degree as to make it lower than that of the organic stream to be washed. As water represents the heavy phase in the countercurrent extractor used for the washing, the feeding to the top of the extractor of this aqueous stream, having a lower density than the organic stream, would prevent its functioning. This aqueous stream cannot even be fed to the bottom of the extractor, using it as light phase, as, once the excess acetone is dissolved in the organic phase, the density of the aqueous stream would increase to a higher value than that of the organic stream and the functioning of the extractor would be equally hindered.

It is therefore necessary to remove the acetone to such a degree as to increase the density of the solution to higher values than the typical value of the organic stream and to enable the remaining water to be fed as solvent into the upper part of the countercurrent extractor without creating flooding problems.

This removal can be conveniently carried out using as solvent the same organic stream leaving the washing and effecting this removal in a tubular device into which the streams are sent in equicurrent.

At the outlet of the mixer, the flow is fed to a decanter to recover the aqueous stream, to be used as washing liquid in the countercurrent extractor, and the organic stream, still containing water, to be sent to a first distillation column to recover a stream containing phenol and high-boiling organic compounds, at the bottom, and a stream containing acetone, water and hydrocarbons, at the top. Alternatively, the organic stream sent to the distillation section is treated in a first column to recover acetone alone, at the head, and then in a second column to recover water and hydrcarbons, at the head, together with the rest of the acetone not recovered in the first column.

The acetone/water/hydrocarbon mixture is, in turn, subjected to decanting to recover the second aqueous stream recycled first to the mixer and subsequently to the extractor as third aqueous stream.

The process for extracting the salts contained in the separated product obtained in the preparation of phenol by the oxidation of cumene of the present invention can be more easily understood by referring to the drawing of the enclosed figure which represents a schematic, illustrative and non-limiting embodiment.

With reference to the drawing, the scheme comprises the extractor E, the mixer M, a first decanter D1, a second decanter D2 and a distillation section represented by the column C, situated between the two decanters.

The organic stream (1) to be subjected to washing, containing acetone and phenol, is fed to the base of the extractor E whereas the washing stream (13) is fed to the head. The stream (13) comprises a recycled aqueous flow (6) and, optionally, a stream of water (12) coming from recovery sections in the plant.

The aqueous phase (4) with the extracted salts, sent for treatment not illustrated in the figure, is recovered from the bottom of the extractor, whereas the washed organic phase (3) in which the content of $Na^+$ ion is substantially reduced, is recovered from the head.

The stream (3) and a recycled stream (11), containing water and acetone, are mixed in M and then subjected to decanting in D1. The aqueous flow (6), fed to the washing, in which the content of acetone is such as to be compatible with the extraction process in E, is recovered from the decanter.

The organic flow (7), taken from D1, still containing water, in which the concentration of salts has been reduced to such a degree as to have an $Na^+$ content of less than 5 mg/l, is sent to the distillation section C, reduced, to simplify the description, to a single column. The stream (9) essentially consisting of phenol and high-boiling products is discharged from the bottom of C.

A stream (8) essentially consisting of water, acetone and hydrocarbons is discharged from the head of C. This is sent to the decanter D2 from which the stream (10), essentially consisting of acetone and hydrocarbons, and the aqueous stream (11) which still contains considerable quantities of acetone, are recovered.

The stream (11) cannot be recycled to the washing as, owing to the presence of acetone, it has a lower density than that of the organic stream (1) to be washed. For this reason the stream (11) is fed to the mixer M where the acetone contained in (11) is partially extracted from the organic stream (3). The aqueous stream thus treated can be used as a washing stream (6) in the extractor E.

What is claimed is:

1. A process for the extraction of the salts contained in the neutralized separated product obtained in the preparation of phenol by the oxidation of cumene which comprises:
   a) feeding the separated product essentially consisting of a stream of phenol and acetone in continuous to an extraction/washing section with water so as to obtain a first aqueous stream containing the extracted products and a first organic stream containing acetone, cumene, phenol and other organic products;
   b) feeding said first organic stream, together with a second recylced aqueous stream containing acetone, to a mixing section;
   c) feeding the stream leaving the mixing section to a first decanting system to obtain a second organic stream and a third aqueous stream;
   d) feeding said third aqueous stream, substantially without acetone, to the washing section of step (a);
   e) feeding said second organic stream to a distillation section to obtain a stream of heavy products essentially consisting of phenol and a stream of light products essentially consisting of water, acetone and hydrocarbons;
   f) feeding the stream of light products to a second decanting system to obtain a third organic stream essentially consisting of acetone and hydrocarbons, and the second aqueous stream which is totally or partially recycled to the mixer of step (b).

2. The process according to claim 1, wherein the washing/extraction of the separated product is carried out in countercurrent using one or more mixers/settlers or a multi-step extractor.

3. The process according to claim 1 or 2, wherein the washing/extraction of the separated product is carried out with a quantity of water ranging from 5 to 10% of the flow-rate of the organic stream.

4. The process according to claim 1, wherein the second aqueous stream essentially consists of 50–65% by weight of water and 35–50% by weight of acetone.

* * * * *